United States Patent [19]

Fujita et al.

[11] Patent Number: 5,031,108
[45] Date of Patent: Jul. 9, 1991

[54] MOLTEN INJECTION-MOLDING METHOD

[75] Inventors: Shigeru Fujita; Susumu Harada, both of Numazu, Japan

[73] Assignee: Toshiba Machine Co., Ltd., Tokyo, Japan

[21] Appl. No.: 272,791

[22] Filed: Nov. 18, 1988

[30] Foreign Application Priority Data

Nov. 27, 1987 [JP] Japan ................................ 62-297857

[51] Int. Cl.$^5$ ........................ G06F 15/31; G05D 7/06
[52] U.S. Cl. .................................... 364/476; 364/578; 425/145
[58] Field of Search ....................... 364/476, 578, 754; 425/145

[56] References Cited

U.S. PATENT DOCUMENTS 4,326,255  4/1982  Fujita ................................... 364/476
4,787,057  11/1988 Hammond ............................ 364/754
4,797,842  1/1989  Nackman et al. .................... 364/578

OTHER PUBLICATIONS

Zienkiewicz: The Finite Element Method, 1977 McGraw-Hill (Textbook) pp. 93/118.
Shephard: Finite Element Modeling in their own Integrated Geometric Modeling Environment Part I: Mesh Generation pp. 61/71.
"Flow Analysis Network (FAN)-A Method for Solving Flow Problems in Polymer Processing", Polymer Engineering and Science, Sep. 1974, vol. 14, No. 9, by Z. Tadmor et al., pp. 660–665.

Primary Examiner—Felix D. Gruber
Attorney, Agent, or Firm—Young & Thompson

[57] ABSTRACT

A molten injection-molding method is applicable to any system of dividing a molded product form model into micro-elements and analyzing a molten material flow behavior within the mold by the use of numerical analytic techniques that include the finite element method, boundary element method, difference method, and FAN method, among others. First, the entire length of time required for the process of filling the mold with a molten material is divided into an arbitrary number of intervals, representing the filling progress in each individual time interval in an equitime curve diagram. This is followed by setting a point that corresponds to any element, drawing from the point a normal line to its corresponding equitime curve, next setting a point of intersection between said normal line and an adjacent equitime curve, drawing another normal line to this equitime curve, and then repeating the series of steps with still other adjacent equitime curves further on, to generate and display a filling flow curve diagram from the points set in correspondence with said equitime curves and normal lines that connect the points together.

5 Claims, 5 Drawing Sheets

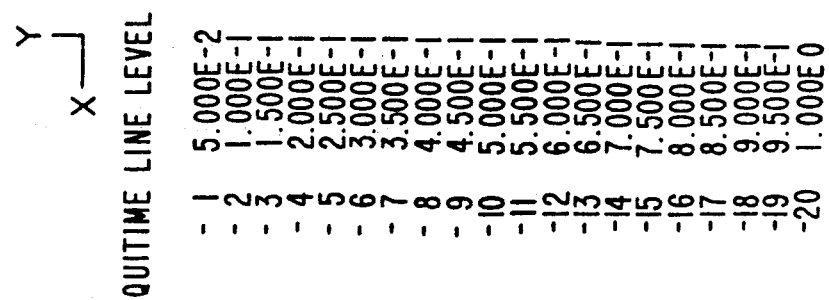
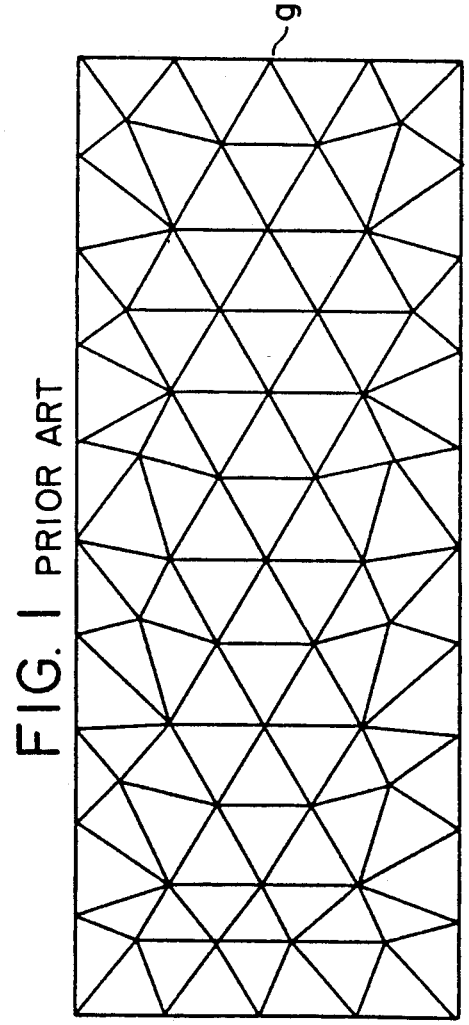
FIG. 1 PRIOR ART
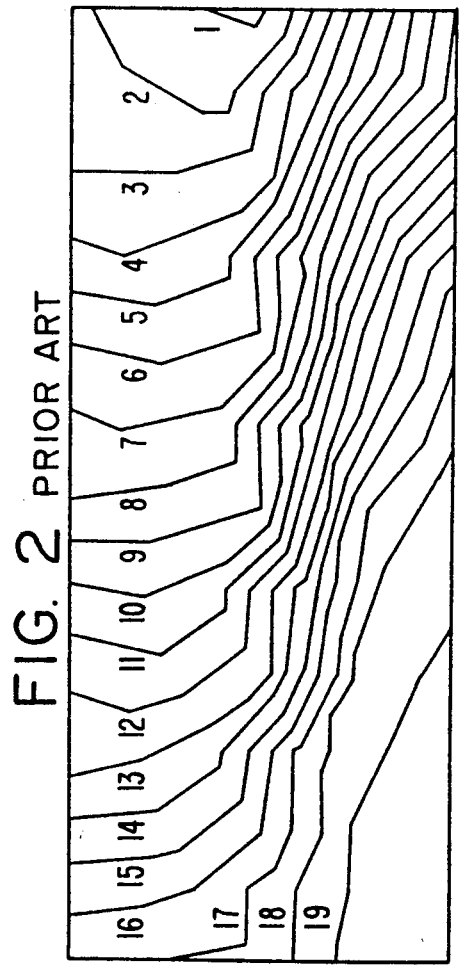
FIG. 2 PRIOR ART

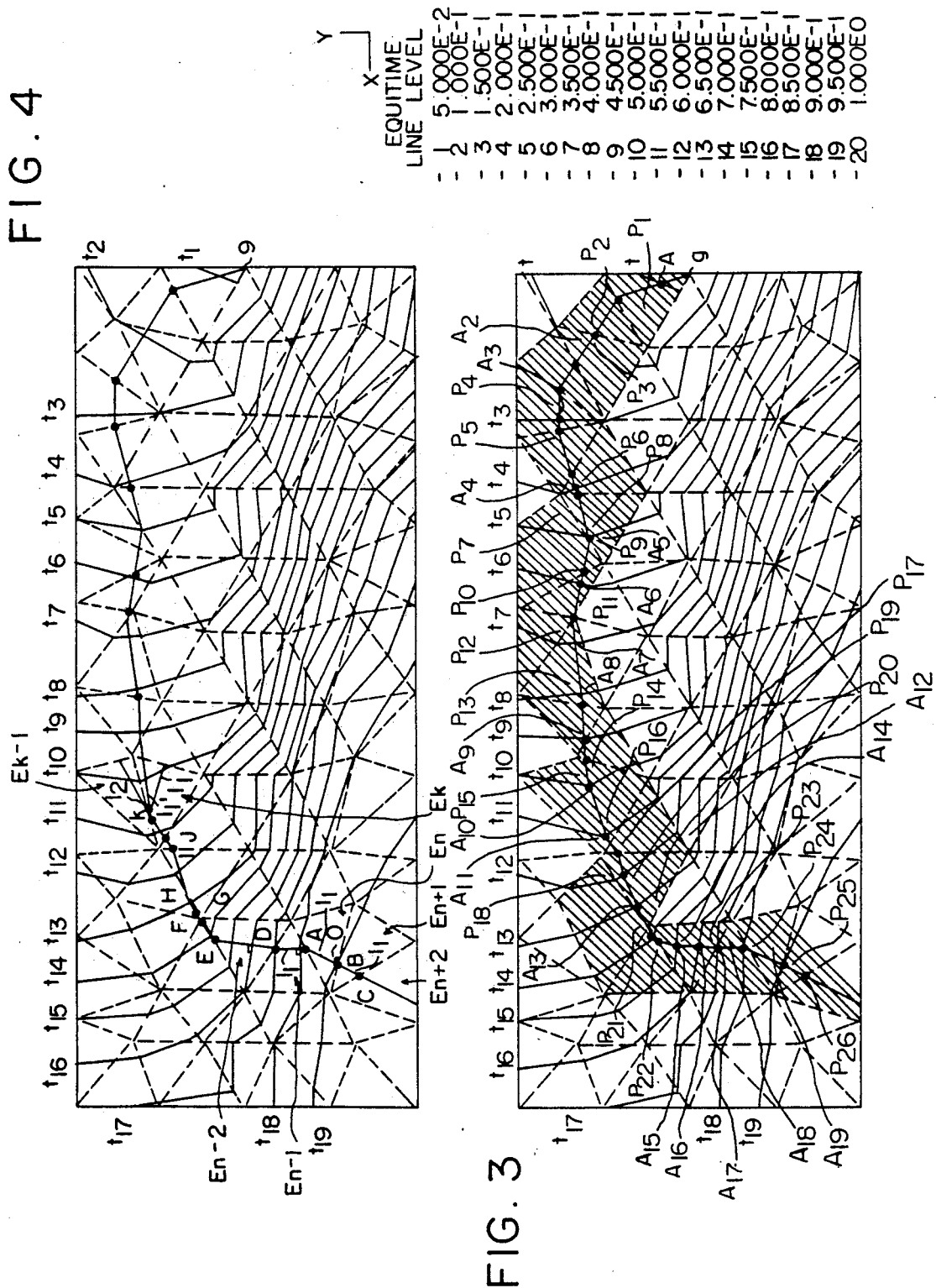

| EQUITIME LINE LEVEL | |
|---|---|
| 1 | 5.000E-2 |
| 2 | 1.000E-1 |
| 3 | 1.500E-1 |
| 4 | 2.000E-1 |
| 5 | 2.500E-1 |
| 6 | 3.000E-1 |
| 7 | 3.500E-1 |
| 8 | 4.000E-1 |
| 9 | 4.500E-1 |
| 10 | 5.000E-1 |
| 11 | 5.500E-1 |
| 12 | 6.000E-1 |
| 13 | 6.500E-1 |
| 14 | 7.000E-1 |
| 15 | 7.500E-1 |
| 16 | 8.000E-1 |
| 17 | 8.500E-1 |
| 18 | 9.000E-1 |
| 19 | 9.500E-1 |
| 20 | 1.000E0 |

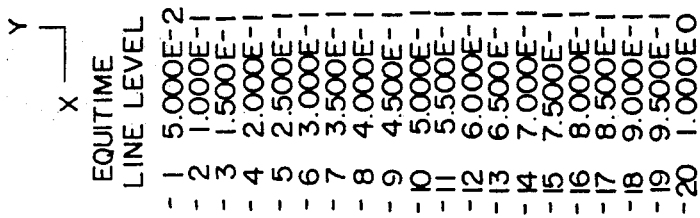
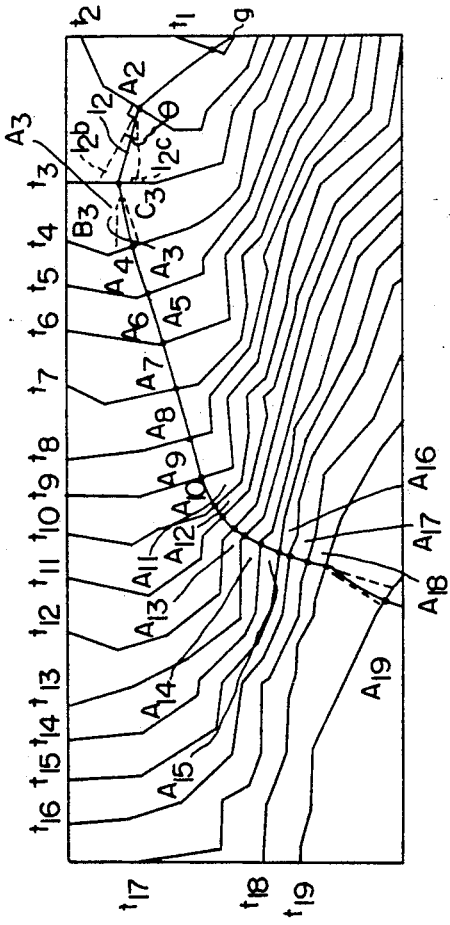
FIG. 8
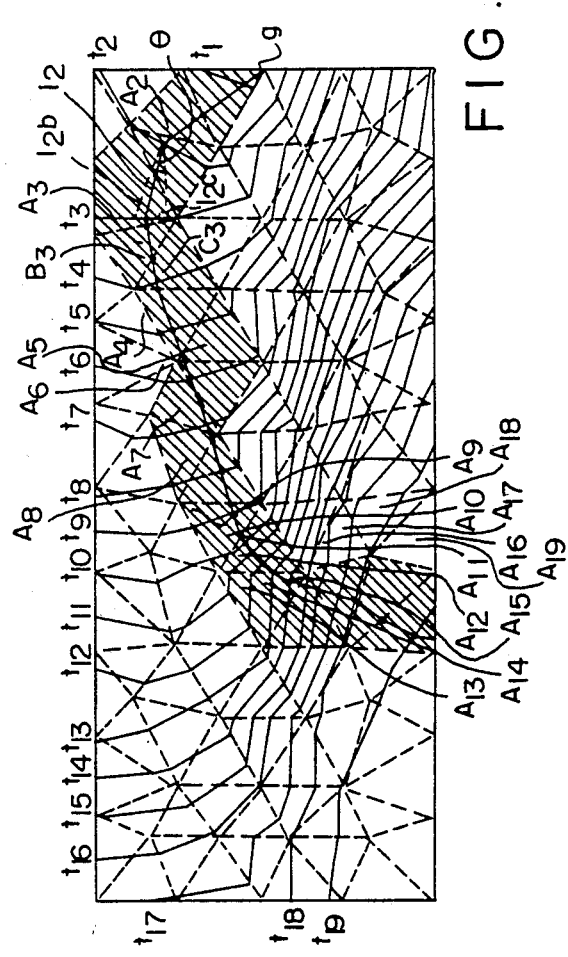
FIG. 7

MOLTEN INJECTION-MOLDING METHOD

FIELD OF THE INVENTION

This invention relates generally with methods to evaluate, and determine, optimum molding conditions for the output of high quality molded products when injection-molding plastic resin and other molten materials, and particularly with methods to judge the acceptability or otherwise of a given status of progress in the filling of a mold with a prescribed molten material.

BACKGROUND OF THE INVENTION

In the conventional intra-mold molten resin flow analysis (simulation) for injection-molding a plastic resin material, an extensively employed approach has been used to divide a form model of the molded product into numerous micro-elements as shown in FIG. 1, and to compute their behavior by solving motional equations, continuity equations, and energy equations of the fluid by the use of a finite element method, boundary element method, difference method, or other numerical analytic techniques.

Under any such intra-mold molten resin flow analytical method, an equitime curve diagram is employed where, as shown in FIG. 2, the time duration of an entire mold filling cycle is broken down into an arbitrary number of constituent intervals, and those of the micro-elements reached by the flow front of a resin at each interval are connected together with line segments as shown in FIG. 2, as a means to express the advancing status of the resin in filling the mold cavity(ies).

The conventional resin flow analytical process mentioned earlier, that is, the method of expressing the mold filling resin advancing status with an equitime curve diagram, is capable of judging whether or not the filling flow of a resin advances well balanced, and whether or not the eventually filled status is satisfactory.

Such an intra-mold resin flow analytical process, however, is disadvantageous in being incapable of judging the appropriateness of any filling speed settings to serve as optimum molding conditions to prevent defective moldings caused by flow turbulences and shearing heat generations due to an excessive resin flow velocity in the filling cycle, and the defective formation of moldings at a specific spot caused by the excessive growth of non-fluid layers. In particular, it has been difficult with equitime curve diagrams alone to judge the effectiveness of programmed injection velocity profile inputs for the multi-level setting of a filling speed against defective moldings at specific spots on the mold.

Accordingly, the objective of this invention is to provide a flow analysis results displaying method for the injection molding of a molten material, with which to facilitate the judgement of adequacy of the advancing status of a molten material being fed to a mold, by utilizing the equitime curve diagram covering a conventional mold fill pattern for the flow analysis of a molten material against a given injection mold.

SUMMARY OF THE INVENTION

The molten injection-molding material flow analysis results displaying method of this invention that, when applied to any system of dividing a molded product form model into micro-elements and analyzing a molten material flow behavior within the mold by the use of numerical analytic techniques that include the finite element method, boundary element method, difference method, and FAN method, among others, wherein first dividing the entire length of time required for the process of filling the mold with a molten material into an arbitrary number of intervals, representing the filling progress in each individual time interval in an equitime curve diagram, making a point setting to correspond to an arbitrary element, drawing from the point just set a normal line to a corresponding equitime curve, next setting a point of intersection between said normal line and an adjacent equitime curve, drawing from the point just set a normal line to said equitime curve, repeating these two steps indefinitely over further point settings, and by connecting said points set against individual equitime curves together with those normal line segments, generating as well as displaying a filling flow curve diagram.

Said displaying method may also be configured by: first selectively setting an arbitrary point within any of the micro-elements of division, drawing a normal line to the equitime curve that corresponds to the micro-element through the point just set, finding the point of intersection between the normal line and the boundary of an adjacent element, next drawing a normal line to the equitime curve that corresponds to the adjacent element containing the point of intersection just found, finding another point of intersection between the normal line just drawn and the boundary with another adjacent element, then repeating the series of steps with that other adjacent element and still other adjacent elements further on, and generating as well as displaying a filling flow curve diagram by connecting together the intersecting points with said individual normal lines set on the boundaries of said individual elements.

A preferable version of said displaying method may be configured by having said individual filling speeds computed through finding the points of intersection between said filling flow curves and individual equitime curves, and through using the linear distances between the intersecting points on each pair of adjacent equitime curves.

Another preferable version of said displaying method may be configured by specifying those of the micro-elements broken down into from a molded product form model that overlap with a part of the filling flow curve, and displaying such micro-element zones for identification.

As an alternative, said displaying method may also be configured to selectively set on any equitime curve a point that corresponds to any element, draw a normal line to the equitime curve from the point, both just set, next, set a point of intersection between said normal line and an adjacent equitime curve, draw another normal line to this equitime curve, then repeat the series of steps with still other adjacent equitime curves further on, and generate as well as display a filling flow curve diagram from the points set in corredspondence with said equitime curves and the normal lines connecting them together.

For the above alternative, too, a preferable version may be configured by specifying those of the micro-elements broken down into from a molded product form model that overlap with a part of the filling flow curve, and displaying such micro-element zones for identification.

Another alternative to said displaying method may be configured to selectively set on any equitime curve a point that corresponds to any element, draw a normal line from the point just set to the equitime curve as well as another straight line that vertically intersects an adjacent equitime curve, draw a bisecting line between these normal and straight lines, next, set a point of intersection between said bisecting line and adjacent equitime curve, draw a bisecting line relative to the next adjacent equitime curve, then repeat the series of steps with still other adjacent equitime curves further on, to generate and display a filling flow curve diagram using the points set against said equitime curves and said bisecting lines that connect these points together.

A preferable version of the above may be configured by having each of the straight lines that vertically intersect said adjacent equitime curves originate from an equitime curve or its extension within the element containing an intersecting point of the normal line to the equitime curve with an adjacent equitime curve.

A preferable version may also be configured by specifying those of the micro-elements broken down into from a molded product form model that overlap with a part of the filling flow curve, and displaying such micro-element zones for identification.

When employing the molten injection-molding material flow analysis results displaying method of this invention, utilizing the equitime curve diagram that represents the filling progress status of a molten material into a mold, drawing a normal line from a point arbitrarily selected on an equitime curve to have it intersect an adjacent equitime curve, and repeating the steps to generate a filling flow curve diagram, a regerence curve meeting predesignated criteria may be defined on said equitime curve diagram, and by displaying it together with those of the divided elements of a molded product form model that are associated with the defined reference curve, the appropriateness of the advancing status of a molten material filling a mold may be made easy to judge. By specifying those of the divided elements that overlap any part of said filling flow curve, and displaying the zones containing those elements in an identifiable form, appropriateness of the progress status of the molten material filling the mold may therefore be made simple to judge.

Described below in depth by referring to attached drawings are some of the example embodiments of the molten injection-molding material flow analysis results displaying method under this invention.

BRIEF DESCRIPTION OF THE DRAWINGS

FIG. 1 graphically illustrates a product form model for injection-molding a molten material that has been divided, or broken-down, into 2-dimensional micro-elements;

FIG. 2 shows the equitime curve diagram of a fill pattern for the form model shown in FIG. 1;

FIG. 3 graphically illustrates the filling flow curves and a series of broken-down element zones of an example embodiment of the molten injection-molding material flow analysis results displaying method under this invention;

FIG. 4 graphically illustrates the analytical process over the filling flow curve shown in FIG. 3;

FIG. 7 graphically illustrates the filling flow curve and a series of broken-down element zones in corresondence therewith of still another example embodiment of the molten injection-molding material flow analysis results displaying method under this invention;

FIG. 8 graphically illustrates the process for analyzing the filling flow curve shown in FIG. 7.

PREFERRED EMBODIMENTS OF THE INVENTION

Figure 6:
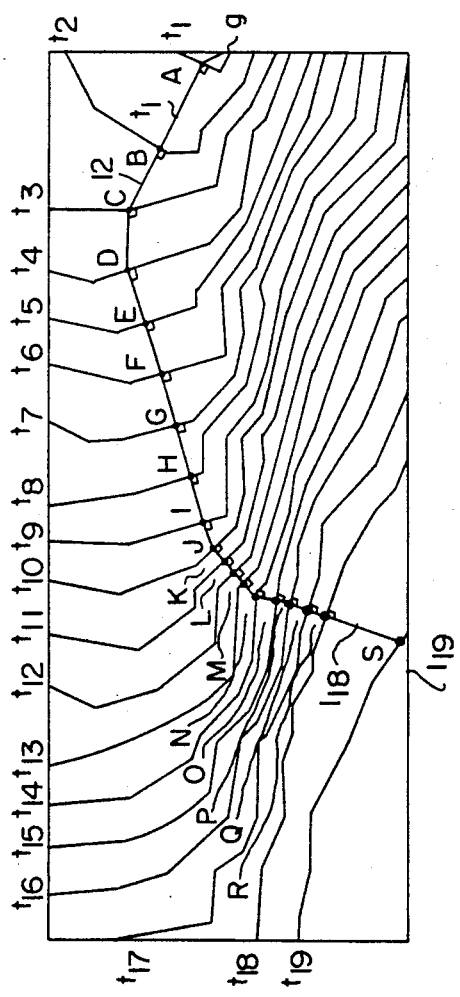
FIG. 6 graphically illustrates the process for analyzing the filling flow curve shown in FIG. 5.

The sequence of steps under this invention to analyze the intra-mold resin flow with regard to a given molded product form model is no different from that employed by the conventional simulation method. Specifically, as shown in FIG. 1, the molded product form model is divided into elements (that have been made triangular in the illustrated example but may just as well be made square or rectangular) for the intra-mold resin flow analysis, and the finite element method is applied to the elements. By making gate locations and quantity settings for the molded product form model and providing runners where required, form settings for the flow analysis may be made complete at the mold end.

Next, a plastic resin for use in molding is selected and its physical property data are input, after which a fill pattern indicating the advancing behavior of a mold-filling resin, or what is known as an equitime curve diagram (see FIG. 2), is duly analyzed. The steps up to this point are identical to those employed for the conventional intra-mold resin flow analysis.

EXAMPLE 1

In this example embodiment, said element breakdown diagram of a molded product form model shown in FIG. 1 and an equitime curve diagram serving as the fill pattern and shown in FIg. 2 are superimposed together and so displayed. Specifically, FIG. 3 shows the display format of this example embodiment, and FIG. 4 an explanatory illustration of the analytical process employed by this sample embodiment for display purposes.

Next, by referring to FIG. 4, the displaying method of this example embodiment is explained below. First, element $E_n$ is arbitrarily selected from among the elements into which the molded product form model has been divided or broken down, and point 0 again arbitrarily set within the element $E_n$ just selected. Next, line 11 is drawn through point 0 just set normal to equitime curve $t_{19}$ that corresponds to element $E_n$, to find points A and B of intersection with the boundary lines of element $E_{n-1}$ and $E_{n+1}$ that are adjacent to said element $E_n$. Then, originating from said intersecting point B, line 11 normal to equitime curve $t_{19}$ is drawn for element $E_{n+1}$, to find point of intersection C of the normal line $1_1$ with the boundary between its adjacent element $E_{n+1}$ and $E_{n+2}$, another element adjacent to $E_{n+1}$.

In the other direction, line 11 normal to equitime curve $t_{18}$ and originating from said point of intersection A is drawn for element $E_{n-1}$, to find point of intersection D of the normal line $1_1$ with the boundary between its adjacent element $E_{n-1}$ and $E_{n-2}$, another element adjacent to $E_{n-1}$.

Thereafter, lines may continue to be drawn for other elements normal to equitime curves that correspond to adjacent elements, to find intersecting points E, F, G, H, I, J and K in that order on relevant inter-element boundaries.

In the example embodiment under discussion, when drawing a line originating from point of intersection K found on the boundary between adjacent elements $E_k$ and $E_{k-1}$, and normal to equitime curve $t_{11}$ that corresponds to point K, the line normal to equitime curve $t_{11}$ corresponding to element $E_{k-1}$ will turn out to be $1_1$ which cannot be drawn within element $E_{k-1}$.

In a case such as the above, not only said normal line $1_1$ but also line 12 normal to equitime curve $t_{11}$ for element $E_k$ are drawn, and a line $1_1$ bisecting the angle formed by the two normal lines is additionally drawn, to find point L of intersection with the boundary with either of the adjacent elements. Situations requiring this procedure occur when, as discussed with intersecting point K, the equitime curve that corresponds to an adjacent element about to be plotted for happens to be oriented only an angle below 90° away from its boundary. In other words, a normal line originating from point K referenced to the equitime curve of one of the adjacent elements is made as valid as another one drawn into the other adjacent element, so that the use of a line bisecting the angle between the two normal lines will serve to average out the two valid normal lines.

Thereafter, further intersecting points may be set on adjacent element boundaries by following similar steps to the foregoing, and by connecting the points together with straight line segments, a single, continuous filling flow curve such as shown in FIG. 4 may be plotted. Incidentally, "g" in the diagram denotes the location of a gate.

Accordingly, by picking out the divided elements that contain any of the individual points of intersection, $P_1$ through $P_{26}$, through which the filling flow curve just plotted passes, a series of element zones such as shown hatched in FIG. 3 may be displayed.

Thus, by this example embodiment, equitime curve diagrams serving as the conventional mold fill pattern may still be utilized to have the resin flow behavior in a mold filling cycle displayed as a reference curve meeting predesignated criteria. In addition, the display may be made to cover a series of zones coinciding with said reference curve containing some of the elements that a molded product form model has been broken down into, facilitating the judgement of adequacy of any resin advancing status in a mold filling cycle.

The analytical processing to make the displays so far discussed possible is simple to achieve by the use of a computer, and the analytically processed results may easily be graphically displayed by the use of a liquid crystal, CRT, plasma, EL, or similar other display equipment.

Incidentally, in the discussion of this example embodiment above, a single arbitrary point, "0", has selectively been set within a divided element corresponding to equitime curve $t_{19}$, but it goes without saying that the point "0" setting may be made in the element corresponding to any equitime curve, and that the point setting may also be varied in any way to have a variety of filling flow curves displayed for the judgement of overall appropriateness. In addition, multiple filling flow curves may also be simultaneously displayed without any problem for overall appropriateness judgements.

EXAMPLE 2

Figure 5:
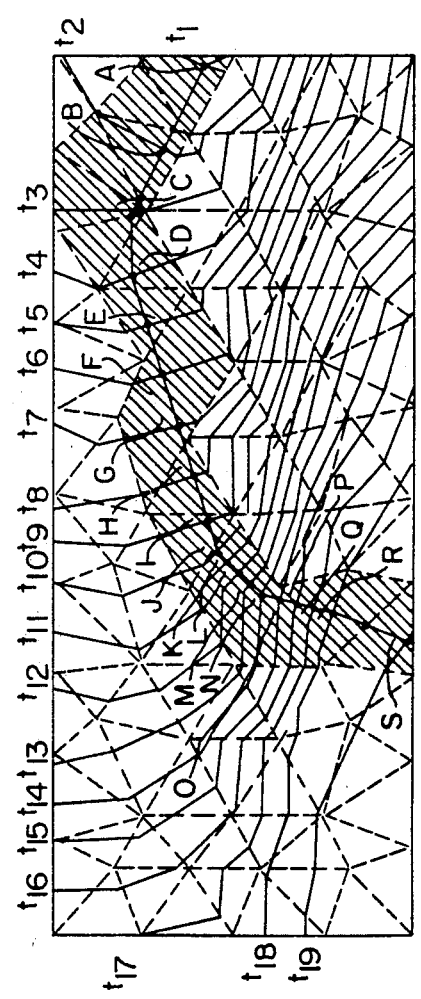
FIG. 5 graphically illustrates the filling flow curves and a series of broken-down element zones in correspondence therewith of another example embodiment of the molten injection-molding material flow analysis results displaying method under this invention.
Figure 9:
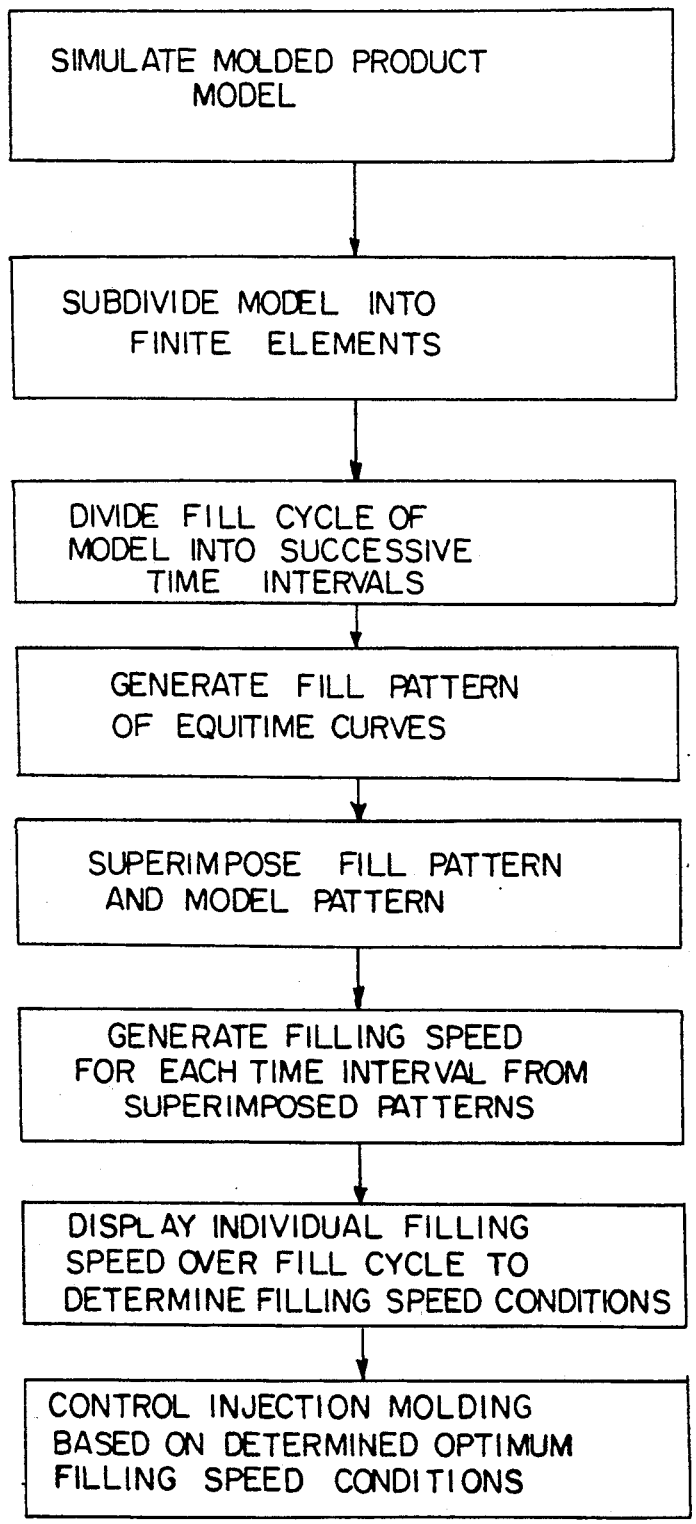
FIG. 9 is a flowchart schematically depicting the overall process according to the invention.

In this example embodiment, said element breakdown diagram for a molded product form model shown in FIG. 1 and an equitime curve diagram shown in FIG. 2 and serving as the fill pattern are superimposed together and so displayed. Specifically, FIG. 5 shows the display format of this example embodiment, and FIg. 6 an explanatory illustration of the analytical process employed by this sample embodiment for display purposes.

Next by referring to FIG. 6, the displaying method of this example embodiment is explained below. First, gate location g through which the mold is filled with a resin is made to serve as the starting point, and after selectively setting point A on the first equitime curve, location g is connected with point A with a straight line segment. Next, normal line $1_1$ is drawn to the first equitime curve $t_1$, originating from said point A, and its intersection with the second equitime curve $t_2$ assigned as point B. Then, normal line $1_2$ is drawn to the second equitime curve $t_2$, originating from said point B, and its intersection with the third equitime curve $t_3$ assigned as point C. Similarly, normal lines $1_3$ through $1_{19}$ are drawn to the third to nineteenth equitime curves $t_3$ through $t_{19}$, and by connecting the normal lines together with line segments, a single, continuous filling flow curve such as shown in FIG. 6 may be plotted.

Accordingly, by picking out the individual divided elements that the thus plotted filling flow curve passes through, a series of element zones such as shown hatched in FIG. 1 may be displayed.

Thus, by this example embodiment, too, not only may appropriateness of the advancing status of a mold filling resin be judged with equal ease to that of said example embodiment 1, but analytically processed results may also be graphically displayed by the use of display equipment, and in addition, by having a variety of filling flow curves displayed, overall adequacy of the resin advancing behavior to accommodate a given form model may be judged as well.

EXAMPLE 3

In this example embodiment, said element breakdown diagram for a molded product form model shown in FIG. 1 and an equitime curve diagram shown in FIG. 2 and serving as the fill pattern are superimposed together and so displayed. Specifically, FIG. 7 shows the display format of this example embodiment, and FIg. 8 an explanatory illustration of the analytical process employed by this example embodiment for display purposes.

Next, by referring to FIG. 8, the displaying method of this example embodiment is explained below. First, equitime curve $t_n$ (the second equitime curve $t_2$ in the illustrated example) and point $A_n$ ($=A_2$) thereon are arbitrarily selected, and normal line $1_{nb}$ ($=1_{2b}$) is drawn to said equitime curve $t_n$ ($=t_2$) originating from said point $A_n$ ($=A_2$) to intersect adjacent equitime curve $t_{n+1}$ ($=t_3$) at a point that will be assigned as $B_{n+1}$ ($=B_3$). In addition, its point of intersection with straight line $1_{nc}$ ($=1_{2c}$) that is normal to said adjacent equitime curve and passing through said point $A_n$ will be assigned as $C_{n+1}$ ($=C_3$). Now, its point of intersection with bisecting line $1_n$ ($=1_3$) of $\angle B_{n+1}/A_n/C_{n+1}$ ($=\angle B_3/A_2/C_3$) is looked for. The bisecting line $1_n$ at $\theta/2$ in angle has one half of the apex angle $\kappa$ of a triangle formed by points $A_n$, $A_{n+1}$, and $C_{n+1}$ as its apexes, and serves to indicate the flow progress of a resin from equitime curve $t_n$ to equitime curve $t_{n+1}$.

Thereafter, by similar steps, line segments bisecting the angles formed by normal lines $1_{nb}$ through $1_{19}b$ to equitime curves $t_n$ through $t_{19}$ passing through points $A_{n+1}$ through $A_n$, and straight lines vertically intersecting adjacent equitime curves $t_{n+1}$ through $t_{19}$ are drawn to reach points assigned as $A_{n+1}$ through $A_{19}$, and by connecting the line segments together, a single, continuous filling flow curve such as shown in FIG. 8 may be plotted. Accordingly, by picking out the individual breakdown elements that the thus plotted filling flow curve passes through, a series of element zones such as shown hatched in FIG. 1 may be displayed.

Thus, by this example embodiment, too, not only may appropriateness of the advancing status of a mold filling resin be judged with equal ease to that of said example embodiment 1, but analytically processed results may also be graphically displayed by the use of display equipment, and in addition, by having a variety of filling flow curves displayed, overall aedquacy of the resin advancing behavior to accommodate a given form model may be judged as well.

As revealed by the example embodiments presented so far, this invention enables, for the flow analysis when filling the mold of a given form model with a molten resin, acquiring a filling flow curve diagram to serve reference purposes, based on an equitime curve diagram that represents the above mold fill pattern, and therewith, easily judging adequacy of the fill pattern that passes through any given specific point. In addition, by displaying a series of element zones that coincide with said filling flow curve when combined with an element broken-down form model, the invention further enables judging the adequacy or otherwise of any resin advancing status in relation to the form model.

Accordingly, by employing this invention for the flow analysis of a resin over a molded product form model, not only may the appropriateness of any molten resin injection velocity (speed) for the output of high quality moldings be judged with ease on a simple graphic display, but based on the judgement outcome, a variety of molding conditions may also be selected from to achieve optimum settings, notably of the injection velocity (speed), making outstanding contributions to the generation of superior programs for the injection-molding of any molten plastic resin.

Although in the example embodiments presented so far, the injection molding method has been discussed in depth, this invention is not limited by such embodiments, but may also be applied to the injection molding of any other molten material than resins, such as for example to die-casting equipment, and may of course be modified for various other applications as well, as long as within the scope and spirit of this invention.

What is claimed is:

1. A method for injection molding a product, comprising the steps of:
   (a) simulating an injection-molded product formed in a mold having a gate through which molten material is injected at an injection velocity during a fill cycle by forming a model of the product;
   (b) generating a model pattern of the model by subdividing the model into a plurality of elements;
   (c) dividing the fill cycle into a plurality of successive time intervals;
   (d) generating a fill pattern of equitime curves, each representative of the advancement over time of the molten material through the mold for respective successive time intervals;
   (e) superimposing the fill pattern over the model pattern;
   (f) generating a filling flow curve over the superimposed patterns, said filling flow curve representing the flow of the molten material from the gate through the mold to a selected location in the mold;
   (g) visually displaying only those elements in the model pattern through which the filling flow curve passes to determine optimum molding conditions at said selected location; and
   (h) controlling an injection molding operation in accordance with the determined optimum conditions.
   (g) visually displaying only those elements in the model pattern through which the filling flow curve passes to determine optimum molding conditions at said selected location; and
   (h) controlling an injection molding operation in accordance with the determined optimum conditions.

2. The method according to claim 1, wherein step (b) is performed by forming each element with linear boundary lines, and wherein step (d) is performed by forming each equitime curve with linear segments.

3. The method according to claim 2, wherein step (f) is performed by selecting a first starting point within a first element associated with a first equitime curve having a first linear segment; determining points of intersection on boundary lines of adjacent second and third elements by extending a normal line through said first point and perpendicular to said first linear segment; interconnecting the intersection points; and repeating said determining step with each intersection point as a starting point until a point of intersection corresponds to the location of the gate.

4. The method according to claim 2, wherein step (f) is performed by selecting a first gate point in a first element associated with a first equitime curve having a first linear segment; selecting a second point in a second element associated with a second equitime curve having a second linear segment; interconnecting the first and second points; determining a point of intersection with a third element by extending a normal line through said second point and perpendicular to said first segment; and repeating said determining step with each intersection point as a starting point until a point on the superimposed patterns corresponds to said selected location in the mold.

5. The method according to claim 2, wherein step (f) is performed by selecting a first starting point on a first linear segment of a first equitime curve; extending a first normal line through said first point and perpendicular to an adjacent second linear segment of a second equitime curve; extending a second normal line through said first point and perpendicular to said first linear segment; determining a second point of intersection on the second equitime curve by extending a bisecting line that bisects the angle included between said first and second normal lines; interconnecting the first and second points; and repeating said extending steps with each point of intersection as a starting point until a point on the superimposed patterns corresponds to said selected location in the mold.

* * * * *